United States Patent

Clissold et al.

Patent Number: 5,112,976
Date of Patent: May 12, 1992

[54] PREPARATION OF 2,6-DIOXOPIPERIDINE DERIVATIVES

[75] Inventors: Derek W. Clissold, Wokingham; John Mann; Christopher P. Thickitt, both of Reading, all of England

[73] Assignee: National Research Development Corporation, London, England

[21] Appl. No.: 701,641

[22] PCT Filed: May 15, 1991

[86] PCT No.: PCT/GB89/00308

§ 371 Date: Sep. 20, 1990

§ 102(e) Date: Sep. 20, 1990

[87] PCT Pub. No.: WO89/09216

PCT Pub. Date: Oct. 5, 1989

Related U.S. Application Data

[63] Continuation of Ser. No. 572,942, Sep. 20, 1990, abandoned.

[30] Foreign Application Priority Data

Nov. 1, 1985 [GB] United Kingdom ............... 8825501
Mar. 22, 1988 [GB] United Kingdom ............... 8806751

[51] Int. Cl.$^5$ ............................................. C07D 213/72
[52] U.S. Cl. ............................................. 546/193
[58] Field of Search ............................. 546/193, 219

[56] References Cited

U.S. PATENT DOCUMENTS 2,673,205 3/1954 Hoffmann et al. ............... 546/219
2,848,455 8/1958 Hoffmann et al. ............... 546/220

FOREIGN PATENT DOCUMENTS 2151226 7/1985 United Kingdom.
2162177 1/1986 United Kingdom.

OTHER PUBLICATIONS

Tet. Letts. (1985) 26 (10) 1311-1314 R. J. P. Corriu et al.
"Reagents for Organic Synthesis" vol. 1 (1967) L. F. Feiser et al. pp. 915-916 John Wiley & Sons. Inc. (New York, U.S.).
Journal of the Chemical Society. Perkin Transactions I (1981) pp. 2476-2482 M. P. Sammes et al.

Primary Examiner—C. Warren Ivy
Assistant Examiner—Catherine Scalzo
Attorney, Agent, or Firm—Nixon & Vanderhye

[57] ABSTRACT

3-Alkyl- or fluoroalkyl-3-(4-pyridyl)piperidine-2,6-diones, useful in the treatment of breast cancer, of formula

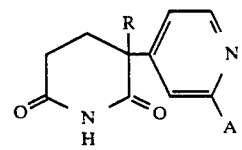

wherein R represents an alkyl group having 2 to 10 carbon atoms or a fluoroalkyl group having 2 to 5 carbon atoms and A is hydrogen or an alkyl group having 1 to 4 carbon atoms, are prepared by reacting a 4-pyridylacetate with an alkyl or fluoroalkyl iodide, chloride or bromide, in the presence of a sterically bulky base and reacting the product with acrylamide in the presence of a sodium or potassium branched chain alkoxide. Preferably potassium t-butoxide is used in both stages and they are carried out sequentially at room temperature in an alcoholic or polar, aprotic solvent in a single reaction vessel.

11 Claims, No Drawings

PREPARATION OF 2,6-DIOXOPIPERIDINE DERIVATIVES

This is a continuation of application Ser. No. 07/572,942, filed Sep. 20, 1990, now abandoned.

BACKGROUND OF THE INVENTION

1. FIELD OF THE INVENTION

This invention relates to the preparation of 3-alkyl- or fluroalkyl-3-(4-pyridyl) piperidine-2, 6-diones of formula (1):

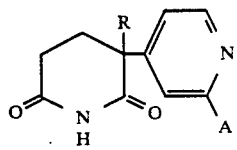

(1)

wherein R represents an alkyl group having 2 to 10 carbon atoms or a fluoroalkyl group having 2 to 5 carbon atoms, and A represents hydrogen or an alkyl group having 1 to 4 carbon atoms, many of which are known compounds, useful in anti-cancer therapy, specifically the treatment of oestrogen-dependent breast tumours.

2. DESCRIPTION OF THE PRIOR ART

The compound of formula (1) wherein R is ethyl and X is hydrogen is 3-ethyl-3-(4-pyridyl)piperidine-2,6-dione, conveniently called "pyridogluthethimide" for short, and is the subject of UK Pat. No. 2151226 B (NRDC). The same patent also covers derivatives thereof wherin A is alkyl of 1 to 4 carbon atoms. Analogues of pyridogluthethimide in which R is an alkyl group having 3 to 10 carbon atoms or a fluoroalkyl group having 2 to 5 carbon atoms are the subject of UK Pat. No. 2162177 B (NRDC).

In UK Pat. No. 2151226 B pyridoglutethimide is prepared by a 3-step process illustrated by Scheme 1 below:

ises on this reaction scheme as involving the cyclisation of a compound of formula (2):

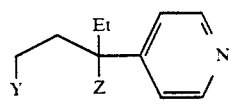

(2)

wherein at least one of Y and Z is cyano or amido and the other, if not also cyano or amido, can be a carboxylic acid group or a non-amide derivative thereof such as an ester. The preparation of compounds of formula (2) in which Y and Z are other than cyano is not described.

UK Pat. No. 2162177 B describes an improved method of carrying out the first step of Scheme 1, in which 4-pyridylacetonitrile is reacted with a primary alcohol, a trivalent rhodium salt and triphenylphosphine under mildly alkaline conditions. This gives the monoalkylated product, substantially free of dialkylated by-product. Other compounds were made using an alkyl bromide or fluoroalkyl iodide and caesium carbonate in the first step of Scheme 1. However, rhodium and caesium salts are relatively expensive reagents.

SUMMARY OF THE INVENTION

It has been found that pyridoglutethimide and its analogues can be prepared in good yield without the use of expensive inorganic salts or other esoteric reagents. In the process of the invention, it has been found possible to avoid production of a dialkylated intermediate and to carry out the whole process in only two reaction steps, which, under preferred conditions, can be carried out sequentially in the same reaction vessel.

The present invention provides a process for the preparation of 3-alkyl- or fluoroalkyl-3-(4-pyridyl)-piperidine-2,6-diones of formula (1):

(1)

Scheme 1

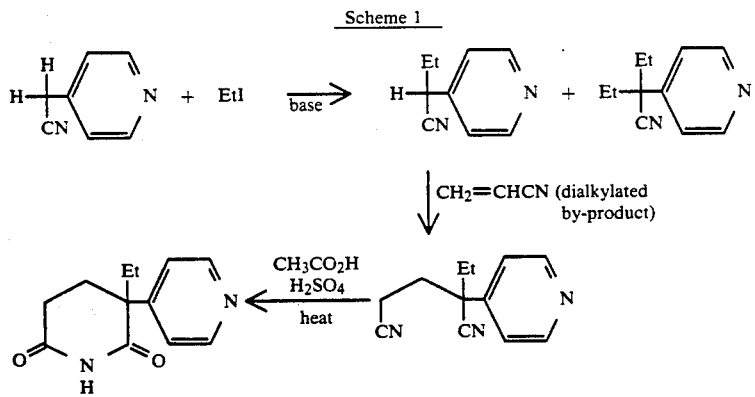

This method of preparation suffers from the disadvantage that the starting 4-pyridylacetonitrile is readily dialkylated, leading to a poor yield requiring a separation step.

In the final stage of Scheme 1, the reaction can be visualised as proceeding by a mechanism in which the cyano groups are hydrolysed to amido groups and then cyclised to single amido group with elimination of a molecule of ammonia. UK Pat. No. 2151226 B general-

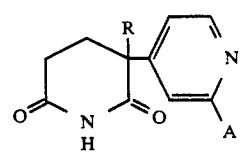

wherein R represents an alkyl group having 2 to 10 carbon atoms or a fluoroalkyl group having 2 to 5 carbon atoms and A represents hydrogen or an alkyl group having 1 to 4 carbon atoms, said process comprising alkylating a 4-pyridylacetic acid alkyl ester, optionally substituted at the 2-position of the pyridine ring by an alkyl group having 1 to 4 carbon atoms, with an alkyl or fluoroalkyl halide of formula RX, X being iodo, bromo or chloro, in the presence of a sterically bulky base of a sodium, potassium or ammonium cation and reacting the product of said alkylation reaction, with acrylamide in the presence of a sodium or potassium branched chain alkoxide, until cyclisation occurs.

What is novel and inventive herein comprises:
(1) the use of a sterically hindering, bulky, but nevertheless predominantly ionic, type of base in the alkylation reaction, so that excessive dialkylation is avoided,
2) reaction of monoalkylated ester with acrylamide, rather than acrylonitrile and
(3) the critical selection of an appropriate base in which to carry out the reaction with acrylamide. (This criticality is explained in more detail below.).

DESCRIPTION OF PREFERRED EMBODIMENTS

The process of the invention is illustrated by Scheme 2 below, which shows the preparation of pyridoglutethimide using potassium t-butoxide, the preferred base, in both the alkylation and acrylamide reaction steps.

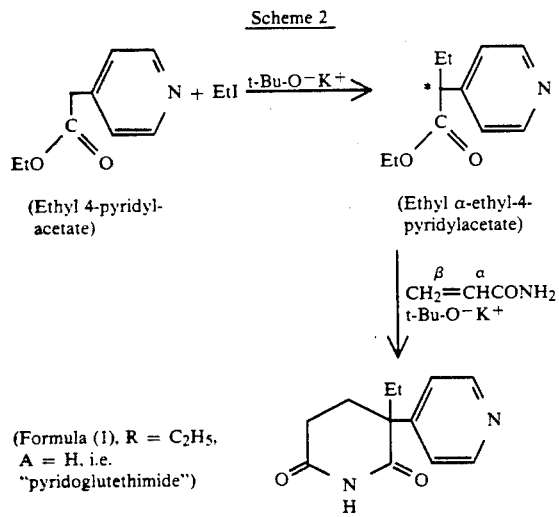

Scheme 2

(Ethyl 4-pyridyl-acetate)

(Ethyl α-ethyl-4-pyridylacetate)

β  α
$CH_2=CHCONH_2$
$t$-Bu-$O^-K^+$ (Formula (I), R = $C_2H_5$, A = H, i.e. "pyridoglutethimide")

Referring to Scheme 2, the starting material shown is ethyl 4-pyridylacetate. This is a compound known in the literature and is obtainable from Lancaster Synthesis Ltd., Morecambe, UK. While the ethyl ester is convenient, any desired alkyl ester can be used, the essential criterion being that the ester group has to be a leaving group in the cyclisation, where it is displaced at the ketonic carbon atom by an amido group. In particular, it can most conveniently be any other alkyl ester in which the alkyl group has 1 to 4 carbon atoms.

The first reaction step is the introduction of the angular alkyl or fluoroalkyl group, conveniently referred to herein as "alkylation". (The term "alkylation" is used herein in this context to cover introduction of an alkyl or fluoroalkyl group and the product is correspondingly referred to as "alkylated" regardlesss of whether the substituent introduced is alkyl or fluoroalkyl). Alkylation is normally carried out using the iodide of the alkyl or fluoroalkyl substituent which it is wished to introduce, the iodide being a better leaving group than bromide or chloride. In the alkylation reaction, the objective is to substitute the alpha-carbon atom, marked with an asterik in Scheme 2, by only a single alkyl or fluoroalkyl group: dialkyl or difluoroalkyl substitution is to be avoided, since this produces an unwanted side-product which at one stage or another has to be separated. It is essentially a question of choosing a base which provides just the right amount of proton abstraction at the alpha carbon atom, whereby the region of the alpha carbon atom becomes somewhat electron rich, enabling it to act as a nucleophile for displacement of halide ion from the alkyl halide. A variety of bases work well in this reaction, especially sodium or potassium branched alkoxides and most especially potassium t-butoxide. Quaternary ammonium hydroxides of formula $R^1R^2R^3R^4N^+OH^-$ where $R^1$ to $R^4$ represent any of a variety of organic radicals can be used. Conveniently $R^1$ is benzyl and $R^2$, $R^3$ and $R^4$, which may be same or different, are straight chain alkyl groups, most conveniently methyl. Benzyltrimethylammonium hydroxide, (commercially available as "Triton B") is particularly preferred. Potassium fluoride, immobilised on alumina, can also be used.

The above-defined base is predominantly ionic. Alkyl lithiums, e.g. butyl lithium, can produce dialkylation or reaction with the ester group. Conventional nitrogenous bases such as triethylamine and diazobicyclooctane (DABCO) do not give any reaction.

The reaction with the base is normally carried out in a solvent. When an alkoxide is used as the base, an alcohol will usually be the most appropriate solvent; otherwise, a polar, non-protic solvent such as dimethyl sulphoxide or dimethylformamide (DMF) is preferred.

Frequently, the reaction can be initiated very easily at room temperature. The reaction temperature is liable to rise rapidly after a short time, since the reaction is exothermic, but this is not harmful if reasonable control is exercised over the rise in temperature. Clearly, an overvigorous reaction which might lead to dialkylation is best avoided. For this purpose, when scaling up the process, we have found it preferable first to dissolve the base such as potassium t-butoxide in the 4-pyridylacetic ester and then to add the iodide to that solution.

The immediate product of the alkylation reaction is an alpha-alkyl-4-pyridylacetic ester. The simpler compounds of this class are known per se.

The second step of the process of the invention is the reaction with acrylamide. After considerable experiment, it has been found that this reaction works best with a sodium or potassium branched-chain alkoxide such as potassium t-butoxide, which, coincidentally, is preferred in the alkylation reaction too. In the result it has been further found that is is possible to carry out the alkylation and reaction with acrylamide sequentially in the same reaction vessel, without isolating the intermediate alpha-alkyl-4-pyridylacetic ester. This feature makes the process of the invention particularly attractive for use on an industrial scale.

Referring now to the acrylamide reaction, this is in principle a quasi-Michael addition, but is particularly tricky for this reason. It is necessary to maintain the electronegativity of the alpha- carbon atom asterisked in Scheme 2, whereby, the slightly electropositive beta-carbon atom of acrylamide will add successfully to the alpha-alkyl 4-pyridylacetic ester. Unfortunately, there is a tendency of bases to abstract a proton from the alpha-carbon atom of acrylamide, leading to unwanted by-products and a diminution in the yield of the desired piperidine-2,6-dione. Thus, quaternary ammonium hydoxides give low yields, potassium fluoride on alumina also produces a relatively poor yield, as do sodium methoxide or ethoxide. On the other hand, alkyl lithiums again react preferentially with the ester group, metal hydrides produce no product and there is no reaction with organic amine bases.

The acrylamide reaction can again be initiaed at room temperature and is again accompanied by an exotherm. Generally, both reactions are conducted at an average temperature within the range −10 to +60° C.

The acrylamide reaction with the branched chain alkoxide base is preferably carried out in an alcoholic solvent, the alcohol usually but not necessarily being the same alcohol as that from which the alkoxide is derived. Potassium t-butoxide in t-butanol is preferred. A polar, aprotic solvent such as DMF is particularly useful when the R group is higher than ethyl.

While the reaction will usually go to completion fairly easily at room temperature and in an alcoholic solvent, it may on occasion be found to proceed under such conditions only as far as an intermediate, the alpha-amidoethyl-alpha-alkyl-4-pyridylacetic acid alkyl ester of formula (3) below:

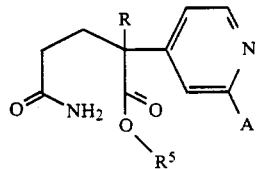

(3)

where $R^5$ represents an alkyl group ($R^5$ is not necessarily the same alkyl group as in the starting 4-pyridylacetic ester, since it is liable to become transesterified with the ester of any alcoholic solvent which may be used, e.g. to become a methyl ester if methanol is used as solvent during isolation of the intermediate of formula (3)).

In case of difficulty in effecting cyclisation in one step, more severe conditions, for example higher temperature or use of an aprotic solvent such as DMF, should be used in this step. If desired, one can, of course, isolate the intermediate and then change the conditions to complete the reaction.

In working up the product, a continuous solvent extraction procedure is preferable and a convenient solvent for that purpose is toluene.

In both the alkylation and the acrylamide reactions; the bases are preferably present in a slight excess, e.g. in an equivalent ratio of 1.1:1 with the starting 4-pyridylacetic ester. In the second reaction, the acrylamide is preferably present in a considerable excess with respect to the 4-pyridylacetic ester or its alpha-alkyl intermediate derivative, as the case may be, an excess of between 20 and 100 percent, preferably about 50 percent, reckoned on equivalents, being preferred.

The process of the invention is particularly applicable to the preparation of compounds of formula (1) in which R is alkyl of 2 to 8 atoms, most especially to pyridoglutethimide.

The following Examples illustrate the invention. Example 6 illustrates the currently most preferred mode of carrying out the process of the invention.

EXAMPLE 1

3-Ethyl-3-(4-pyridyl)piperidine-2,6-dione ("pyridoglutethimide")

Ethyl 4-pyridylacetate (5.0 g, 30 mmol) and ethyl iodide (2.4 ml, 30 mmol) were stirred in dry t-butanol under argon. The flask was placed in a water bath at 20° C. Potassium t-butoxide (4.02 g, 33 mmol) was added. The reaction was exothermic and in 2 min. the temperature rose to 58° C. and then started to fall. After 40 minutes acrylamide (3.20 g, 45 mmol) was added, follwed by potassium t-butoxide (4.02 g, 33 mmol). There was a small exotherm, the temperature rising from 20 to 32° C.

After 30 min. the reaction was worked-up as follows. Water (20 ml) was added, followed by 2 M HCL (18 ml), to give pH 7.0–8.0. Saturated brine (40 ml) was added and the solution was extracted with ethyl acetate (3×80 ml). The combined organic extracts were washed with saturated brine (40 ml), dried over magnesium sulphate and evaporated to give a slightly yellow solid. This solid was recrystallised twice from isopropanol to give white crystals of pyridoglutethimide (3.65 g, 56%), m.p. 134–136° C. (UK Pat. No.s 2151226 B and 2162177 B and Foster et al., J. Med. Chem. 28, 200–204 (1985): 138–139° C.). NMR δ (CDCL$_3$) 0.87 (t, J=7Hz, 3H, Me,CH$_2$), 1.80–2.80 (M, 6H, MeCH$_2$, and H-4,4 and H-5,5), 7.15 (m, 2H, H-3 and H-5 of pyridine ring), 8.55 (m, 2H, H-2 and H-6 of pyridine ring, 9.10 (br. s, 1H, NH), in agreement with Foster et al., supra.

EXAMPLE 2

This Example shows that the process can be carried out, although with a low yield, using a KF/alumina basic catalyst. Ethyl-4-pyridyl acetate (0.5 g, 3 mmole), ethyl iodide (0.25 ml, 3 mmole), and KF alumina (3.65 g, ca. 15 mmole of KF) were stirred in DMF (10 ml) at room temperature under nitrogen for 2 hours. (The KF/alumina base was prepared by mixing KF with a large excess of alumina in water and evaporating off the water). Diethyl ether was added, and the mixture extracted with water (×20 ml), and the ether layer dried and then concentrated to yield 175 mg of the desired monoethylated product (30% yield).

EXAMPLE 3

This example shows that the process can be carried out, although with a low yield, using the quaternary ammonium hydroxide "Triton B". Ethyl-4-pyridyl acetate (0.5 g, 3 mmole), ethyl iodide (0.25 ml, 3 mmole), and "Triton B" (0.5 ml, 40% solution in methanol) were stirred in DMF (10 ml) under nitrogen at room temperature for 1 hour. The reaction mixture was worked-up as before to provide 200 mg of the desired monoethylated product (approx. 35% yield).

EXAMPLE 4 (COMPARATIVE)

This example shows that use of sodium ethoxide as the strong base gives a mixture of mono- and di- ethylated products. Ethyl-4-pyridyl acetate (0.5 g, 3 mmole) and ethyl iodide (0.25 ml, 3 mmole) were stirred in dry t-butanol under nitrogen at room temperature in the presence of sodium ethoxide (0.25 g, 35 mmole). After 1.5 hour, the reaction was worked up as before to yield a mixture of the monoethylated and diethylated products (ratio 2:1, total yield 45%).

EXAMPLE 5

3-Octyl-3-(4-pyridyl)piperidine-2.6-dione

Ethyl 4-pyridylacetate (5.00 g, 30 mmol) and n-octyl iodide (7.90 g, 33 mmol) were stirred in dry t-butanol (100 ml) under nitrogen. The flask was placed in a water bath at 20° C. before potassium t-butoxide (4.02 g, 33 mmol) was added. An exothermic reaction was noted. After 40 minutes, acrylamide (3.20 g, 45 mmol) was added, followed by potassium t-butoxide (4.02 g, 33 mmol). Another, smaller, exothermic reaction was noted. After one hour the reaction was worked-up as described in Example 1 to give a yellow oil. This oil was flash-chromatographed on a silica gel column, eluting with diethyl ether:petrol (19:1 v/v) to remove any unreacted ethyl 4-pyridylacetate and octyl iodide.

The uncyclised product was removed from the column by elution with pure (AnalaR) methanol, thereby forming the methylester derivative at the same time. This was concentrated, taken up in dry DMF (50 ml) and potassium t-butoxide (4.02 g, 33 mmol) added. The reaction mixture was stirred overnight at room temperature, before acidification to pH 5-6 with 2 M HCl. After a further two hours stirring, the mixture was worked-up.

Water (40 ml) was added, before extraction into ethyl acetate (3×50 ml). Drying over magnesium sulphate and concentration gave a gummy yellow oil (6.20 g, 68%). This was crystallised from pentane giving a white solid, m.p. 58° C. (Leung et al., J. Med. Chem. 30, 1550-1554 (1987): 60-62° C.).

NMR δ (CDCL$_3$) 0.87 (t, J=7Hz, 3H, MeCH$_2$—), 1.24 (s, 12H, Me(CH$_2$)$_6$—), 1.8—2.1 (m, 2H, CH$_2$—C—), 2,3—2.80 (m, 4H, H-4,4 and H-5,5), 7.26 (m, 2H, H-3 and H-5 of pyridine ring), 8.64 (m, 2H, H-2 and H-6 of pyridine ring), 9.37 (br. s, 1H, NH).

EXAMPLE 6

3-Ethly-3-(4-pyridyl)piperidine-2,6-dione("pyridoglutethimide")

Ethyl 4-pyridyl acetate (100 g., 0.6 mole) was dissolved in tert-butanol (1000 ml). Potassium tert-butoxide (80 g. 0.66 mole) was added portionwise to the stirred solution. The solution became yellow and there was a rise in temperature of a few degrees. Once the potassium tert-butoxide was fully dissolved, ethyl iodide (48 ml, 0.6 mole) was added dropwise. The temperature rose to about 45° C., and the mixture was stirred over a period of 1.5 hours, during which the temperature returned to room temperature. Acrylamide (64 g., 0.9 mole) was then added together with a further 500 ml of tert-butanol. This was followed by potassium tert-butoxide (80 g. 0.66 mole), and there was a slight rise in temperature. The reaction mixture was stirred for a period of 2.5 hours.

Water (400 ml) was added to the reaction mixture and it was then neutralised to (pH 7-8) with 4N HCl. The total mixture was now continuously extracted with hot toluene overnight (20 hours), and the toluene extract reduced in volume to induce crystallisation. The crude product weighed 80 g, and after one recrystallisation from isopropanol yielded 61 g. (ca. 46%) of pure pyridoglutethimide.

We claim:

1. A process for the preparation of 3-alkyl- or fluoroalkyl-3-(4-pyridyl)piperdine-2,6-diones of formula (1):

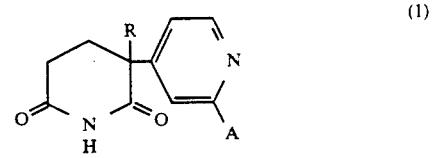

wherein R represents an alkyl group having 2 to 10 atoms or a fluoroalkyl group having 2 to 5 carbon atoms and A represents hydrogen or an alkyl group having 1 to 4 carbon atoms, said process comprising alkylating a 4-pyridylacetic acid alkyl ester of formula (4):

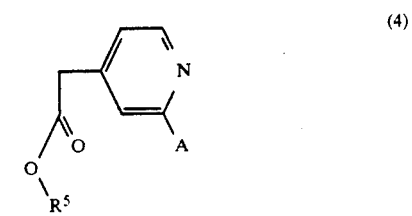

wherein R$^5$ represents an alkyl group and A is defined above, with an alkyl or fluoroalkyl halide of formula RX, X being iodo, bromo or chloro, in the presence of a sterically bulky base of a sodium, potassium or ammonium cation, and reacting the product of said alkylation reaction with acrylamide, in the presence of a sodium or potassium branched chain alkoxide, until cyclisation occurs.

2. A process according to claim 1 wherein the alkylation reaction is carried out in the presence of (a) a sodium or potassium alkoxide or quaternary ammonium hydroxide or (b) potassium fluoride on alumina.

3. A process according to claim 1 wherein the alkylation reaction and the reaction with acrylamide are both carried out in the presence of a sodium or potassium salt of a branched-chain alkoxide having from 3 to 5 carbon atoms.

4. A process according to claim 3 wherein the branched-chain alkoxide is potassium t-butoxide.

5. A process according to claim 3 in which the alkylation and reaction with acrylamide are carried out sequentially in the same reaction vessel.

6. A process according to claim 4, in which the alkylation and reaction with acrylamide are carried out sequentially in the same reaction vessel.

7. A process according to claim 3 wherein the alkylation and reaction with acrylamide are carried out at room temperature and in an alcohol or a polar, nonprotic solvent.

8. A process according to claim 1, wherein R represents an alkyl group of 2 to 8 carbon atoms.

9. A process according to claim 1, wherein X represents iodo.

10. A process acccording to claim 1, 2, 3, 4, 5 or 6 8 wherein the alkylation reaction the base is dissolved in the 4-pyridylacetic acid ester and the iodide is added to that solution.

11. A process according to claim 2, wherein the sodium or potassium alkoxide is a sodium or potassium branched chain alkoxide.

* * * * *

UNITED STATES PATENT AND TRADEMARK OFFICE
CERTIFICATE OF CORRECTION

PATENT NO. : 5,112,976

DATED : May 12, 1992

INVENTOR(S) : CLISSOLD et al

It is certified that error appears in the above-identified patent and that said Letters Patent is hereby corrected as shown below:

Column 8 line 60, claim 10 line 1, delete "1, 2, 3, 4, 5 or 68", and replace by --1, 2, 3, 4, 5, 6 or 8--

Signed and Sealed this

Twenty-third Day of November, 1993

*Attest:*

BRUCE LEHMAN

*Attesting Officer*   *Commissioner of Patents and Trademarks*